(12) United States Patent  
Jin

(10) Patent No.: US 10,527,540 B2  
(45) Date of Patent: Jan. 7, 2020

(54) SMARTPHONE LENS SYSTEM ATTACHMENT

(71) Applicant: Purdue Research Foundation, West Lafayette, IN (US)

(72) Inventor: Jian Jin, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 14 days.

(21) Appl. No.: 15/893,189

(22) Filed: Feb. 9, 2018

(65) Prior Publication Data

US 2019/0331590 A1  Oct. 31, 2019

Related U.S. Application Data

(60) Provisional application No. 62/456,994, filed on Feb. 9, 2017.

(51) Int. Cl.
| | | |
|---|---|---|
| *G01N 21/01* | (2006.01) | |
| *G02B 27/02* | (2006.01) | |
| *G01N 21/27* | (2006.01) | |
| *G03B 17/56* | (2006.01) | |
| *H04M 1/725* | (2006.01) | |
| *G01N 21/84* | (2006.01) | |

(52) U.S. Cl.
CPC .......... *G01N 21/01* (2013.01); *G01N 21/274* (2013.01); *G02B 27/028* (2013.01); *G03B 17/56* (2013.01); *G01N 2021/8466* (2013.01); *H04M 1/72527* (2013.01)

(58) Field of Classification Search
CPC ................ G01N 21/01; G01N 21/274; G01N 2021/8466; G03B 17/56; G02B 27/028; H04M 1/72527
See application file for complete search history.

(56) References Cited

U.S. PATENT DOCUMENTS

| | | | |
|---|---|---|---|
| 2011/0228097 A1* | 9/2011 | Motta | H04N 5/33 348/164 |
| 2016/0156829 A1* | 6/2016 | Takamori | H04N 5/23203 348/207.1 |
| 2017/0176341 A1* | 6/2017 | Mugrabi | G01N 21/01 |
| 2019/0234799 A1* | 8/2019 | Dorier | G01J 3/0229 |

* cited by examiner

*Primary Examiner* — Nirav G Patel  
(74) *Attorney, Agent, or Firm* — Purdue Research Foundation

(57) ABSTRACT

An imaging system for a smartphone includes a housing configured to rigidly attach to a handheld smartphone device. The system further includes an arm extending from the housing, wherein the arm is configured to be adjustable such that the arm is movable toward and away from the housing. Additionally, the system includes a sample mounting portion attached to the arm, the mounting portion having a retaining device, wherein the retaining device is configured to secure a target sample, the mounting portion configured to direct an image of the target sample to a first camera in the handheld smartphone device.

17 Claims, 9 Drawing Sheets

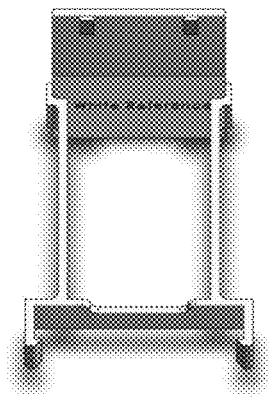
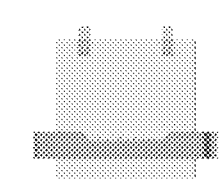 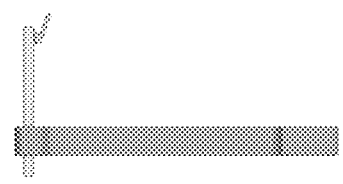 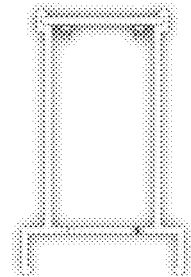
*FIG. 5a*   *FIG. 5b*   *FIG. 5c*

US 10,527,540 B2

SMARTPHONE LENS SYSTEM ATTACHMENT

PRIORITY

The present application is a non-provisional application of U.S. Provisional Application 62/456,994 filed Feb. 9, 2017, titled "SMARTPHONE LENS SYSTEM ATTACHMENT FOR PLANT HEALTH ANALYSIS." the priority of which is hereby claimed and the disclosure of which is hereby incorporated by reference.

TECHNICAL FIELD

The present application relates to plant health analysis, and more specifically, to a system which provides multi-spectral capability for a handheld smartphone device and associated processing to determine the health of a plant foliage sample.

BACKGROUND

Multispectral cameras have been developed for use in various research and industry areas. There are several different ways to implement a multispectral camera, including: 1, with a spectral grating (same as a push-broom hyperspectral camera) 2, with tunable or replaceable filters in front of the lens 3, using filters at the pixel level (similar to an RGB camera, but with more than 3 types of filters) and 4, multiple sensors combined together (commonly used in remote sensing applications). All these methods are either very expensive, slow to take images, or hard to calibrate. Modern smartphones and other handheld devices have incorporated standard RGB cameras, however, they are typically limited in the color bands they can sense and are not typically suitable for multispectral imaging for plant health analysis. Therefore, improvements are needed in the field.

SUMMARY

According to one aspect, the present disclosure provides a smartphone attachment comprising a lens system, the lens system is composed of multiple lenses which allow the camera to simultaneously capture multiple image copies of an object of interest, with one image copy captured through each lens. A plurality of selected filters is applied to each of the corresponding lenses. Calibration is performed by a computer processor in the smartphone, the calibration implements a pixel-to-pixel match between the image copies from the multiple lenses. In this way the system captures a multispectral image with just one shot of the camera, and with much lower cost than prior art solutions. For example, if the lens system is composed of 4 lenses, the system can collect a multispectral image of 4*3=12 bands with an RGB sensor.

BRIEF DESCRIPTION OF THE DRAWINGS

FIG. 5a illustrates a first view of a leaf holder attachment according to one or more embodiment.

FIG. 5b illustrates a second view of a leaf holder attachment according to one or more embodiment.

FIG. 5c illustrates a third view of a leaf holder attachment according to one or more embodiment.

DETAILED DESCRIPTION

In the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

The system of the present disclosure adds additional independent color bands to the existing RGB sensitivity of cameras found in most smartphones, thereby improving sensitivity and precision of plant stress and nutrition level prediction. According to one embodiment, a color band only in the near infrared wavelengths (>700 nm) is added, which provides the needed improvement. Combining the features of available filters and a smartphone camera's quantum efficiency, in one example it was determined that a low pass frequency filter with cutting off edge at 720 nm is well suited for most smartphone brands (Apple, Samsung Galaxy, LG).

Figure 1:
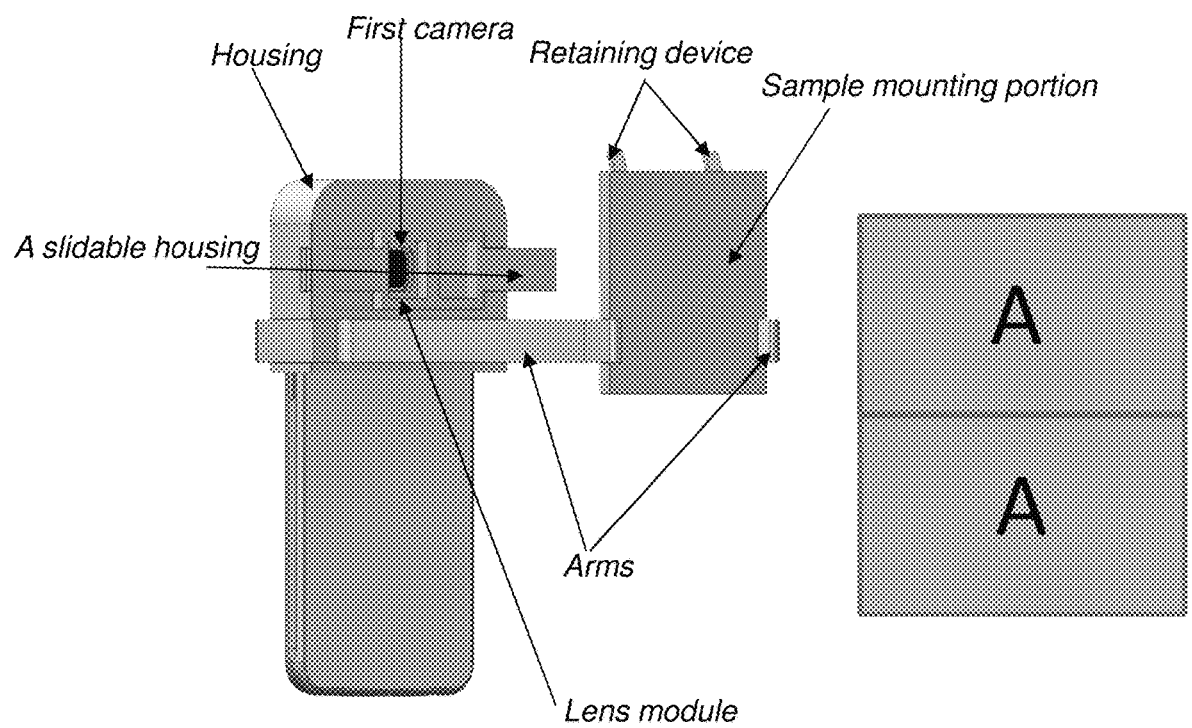
FIG. 1 illustrates one embodiment of a multispectral imaging system in accordance with one or more embodiments.

FIG. 1 shows one embodiment of a multispectral imaging system having a slidable housing with multiple imaging windows in front of the camera of the smartphone. A different filter is applied for each window. When sliding the slidable housing through, the software running on the smartphone (or a connected computer) will automatically capture the images when each window is in front of the camera. The multiple images through multiple windows will be combined by the APP to construct a multispectral image. In certain embodiments, the software is configured to: 1) synchronize the smartphone camera to work together with an attached system (such as system 100 described below) to capture the images. 2) combine the multiple images by pixel-to-pixel matching, and constructs a new multispectral image, 3) conduct image processing algorithms including segmentation (green leaf area detection), averaged leaf spectra calculation, distribution mapping, and so on, 4) apply nitrogen, water, and chlorophyll prediction models and leaf indices formulas to the calculated spectra and generate plant diagnose results, 5) feed back the geo-referenced image file and prediction results back to a GIS database server for further data analysis and services, such as regional crop growth monitoring, yield prediction, and ground truth validation for remote sensing data.

Figure 2:
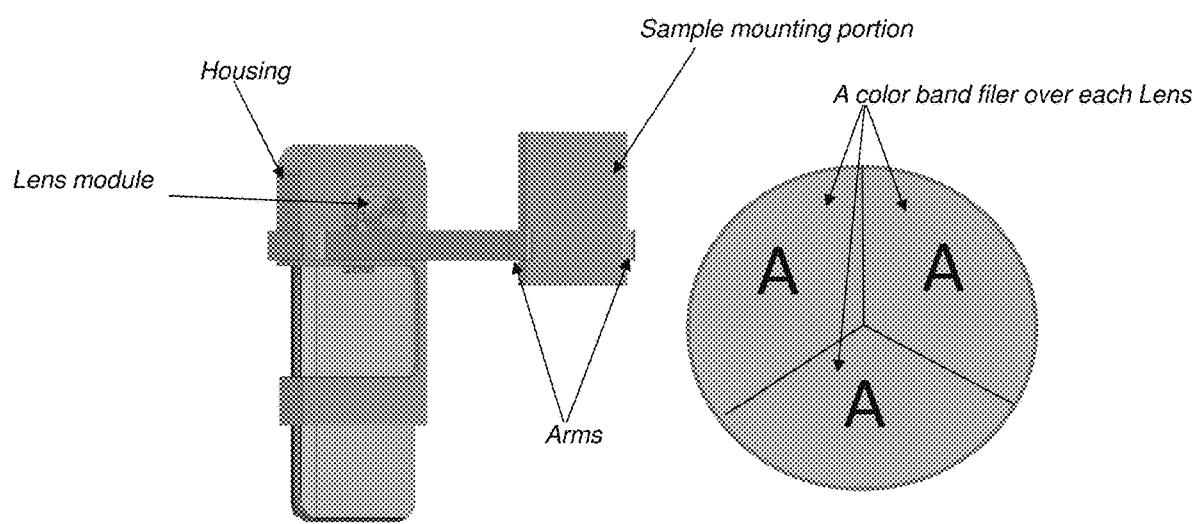
FIG. 2 illustrates a further embodiment of a multispectral imaging system having a multiple lens module mounted in front of the camera.

FIG. 2 shows a further embodiment of a multispectral imaging system having a multiple lens module mounted in front of the camera. The multispectral imaging system further includes a plurality of arms extending from a main housing to a sample mounting portion, wherein the main housing being configured to mount to a handheld smartphone. A different color band filter is applied on each of the lenses of the multiple lens module. In at least one embodiment, the multiple lens module includes three lenses. In the multiple lens module with 3 lenses, each shot of the camera will simultaneously capture 3 images of the same object with different filters. These images will be matched pixel-to-pixel and form the multispectral image by the computer processor within the smartphone. In at least one embodiment, each arm of the plurality of arms is configured to be adjustable such that the each arm is movable toward and away from the camera. The arms are adjusted to cater to various cell phone models and leaf samples/species. In one or more embodiments, each sub-lens of the multiple lens module is positioned and oriented such as to direct the reflected light from a target sample into the camera. In at least one embodiment, the multiple lens module includes multiple sub-lenses and replaceable color filters, wherein each replaceable color filter corresponds to each sub-lens of the multiple sub-lenses. In some embodiments, the replaceable color filters comprise at least one of infrared color filters, UV color filters, or visible color filters. In some embodiments, each sub-lens of the multiple sub-lenses are independent.

Figure 3:
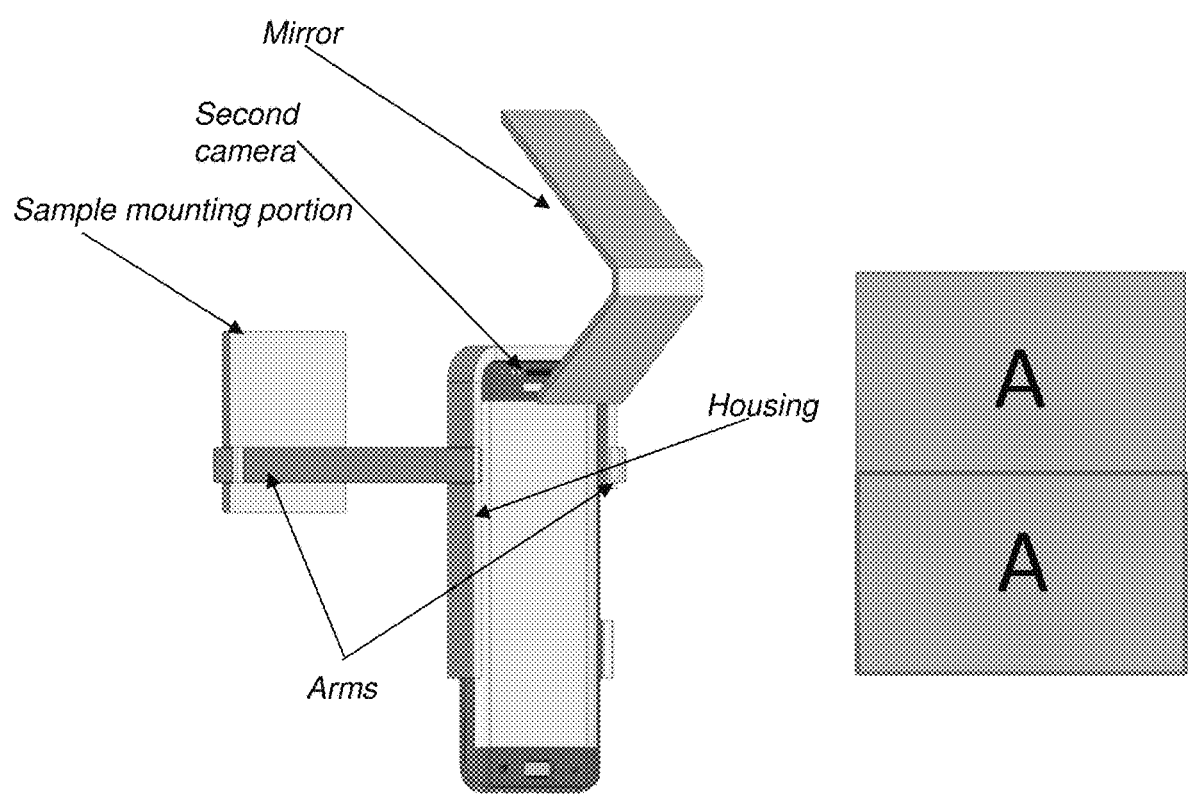
FIG. 3 illustrates a further embodiment of a multispectral imaging system having an extension arm with a mirror.

FIG. 3 shows a further embodiment of a multispectral imaging system having an extension arm with a mirror, allowing the system to direct images to both the front and back cameras of the smartphone. Two different color band filters are applied to each camera so 3×2=6 (in one example) bands are collected. Images are also combined by pixel-to-pixel match to form the multispectral image. In at least one embodiment, a size of the mirror, a distance between the mirror and a sample, and an orientation of the mirror with respect to the sample are configured to reflect light from the sample to the front camera. In some embodiments, the distance between the mirror and a sample, and the orientation of the mirror with respect to the sample are adjustable.

Figure 4:
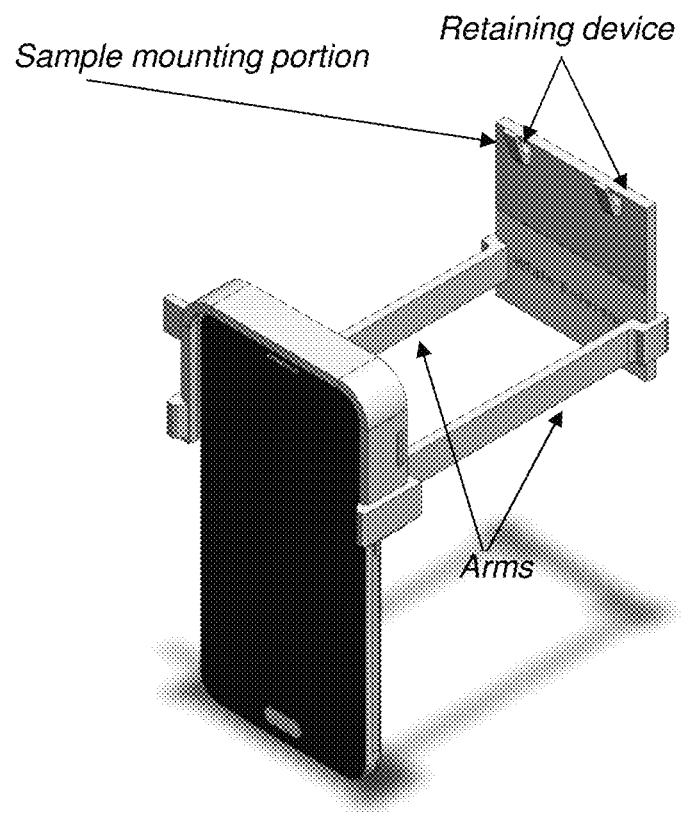
FIG. 4 illustrates a leaf holder attachment according to one or more embodiments.
Figure 6:
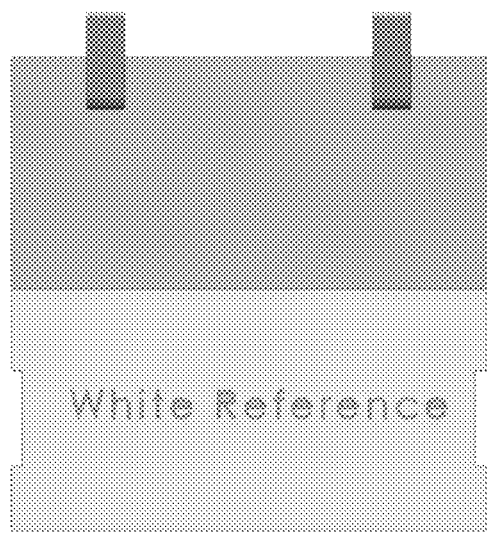
FIG. 6 illustrates a leaf holder attachment according to one or more embodiments.
Figure 7:
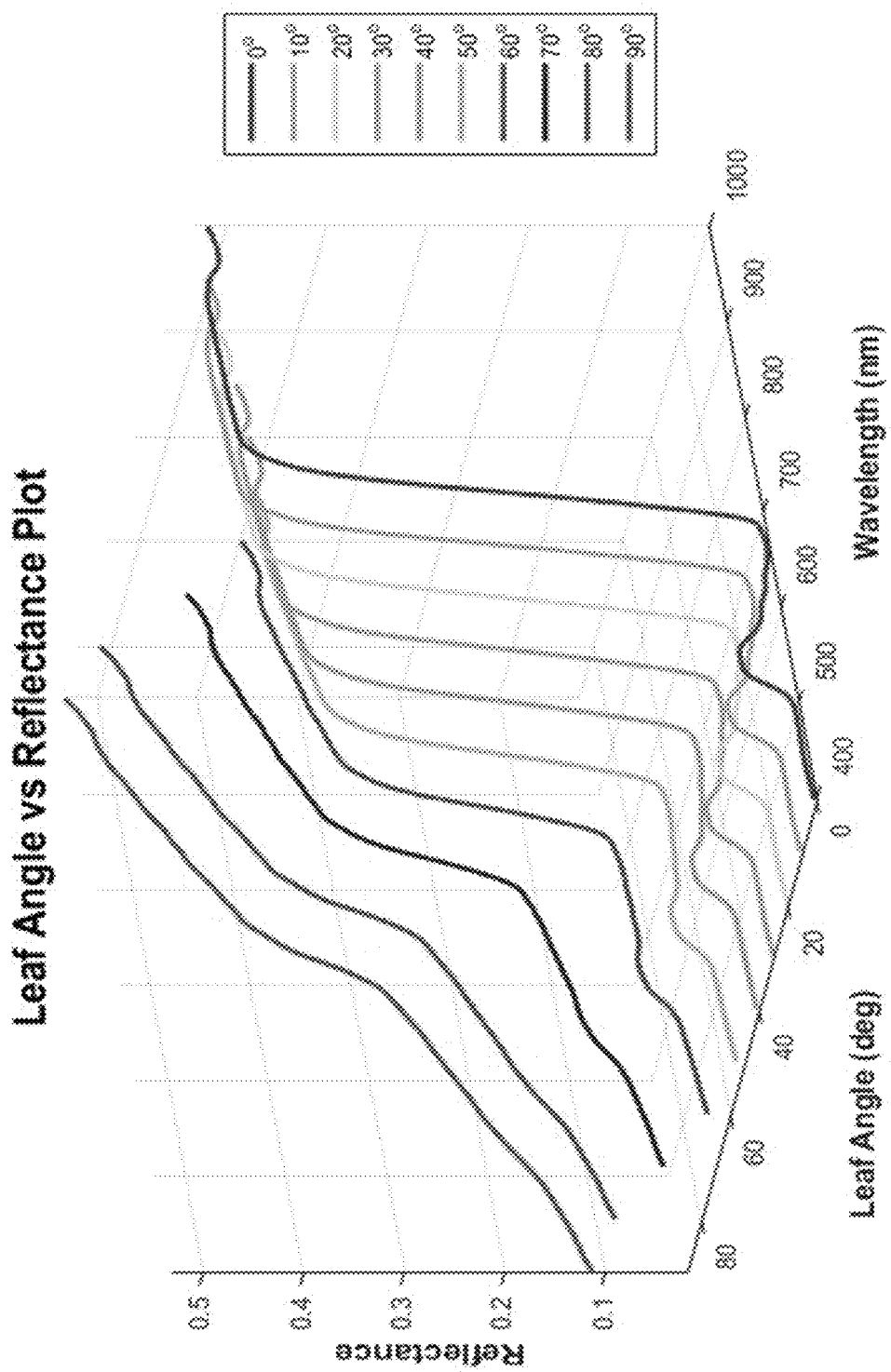
FIG. 7 illustrates the relative angle between the leaf surface (e.g., from 0 degrees to 80 degrees) and the camera's normal direction.
Figure 8:
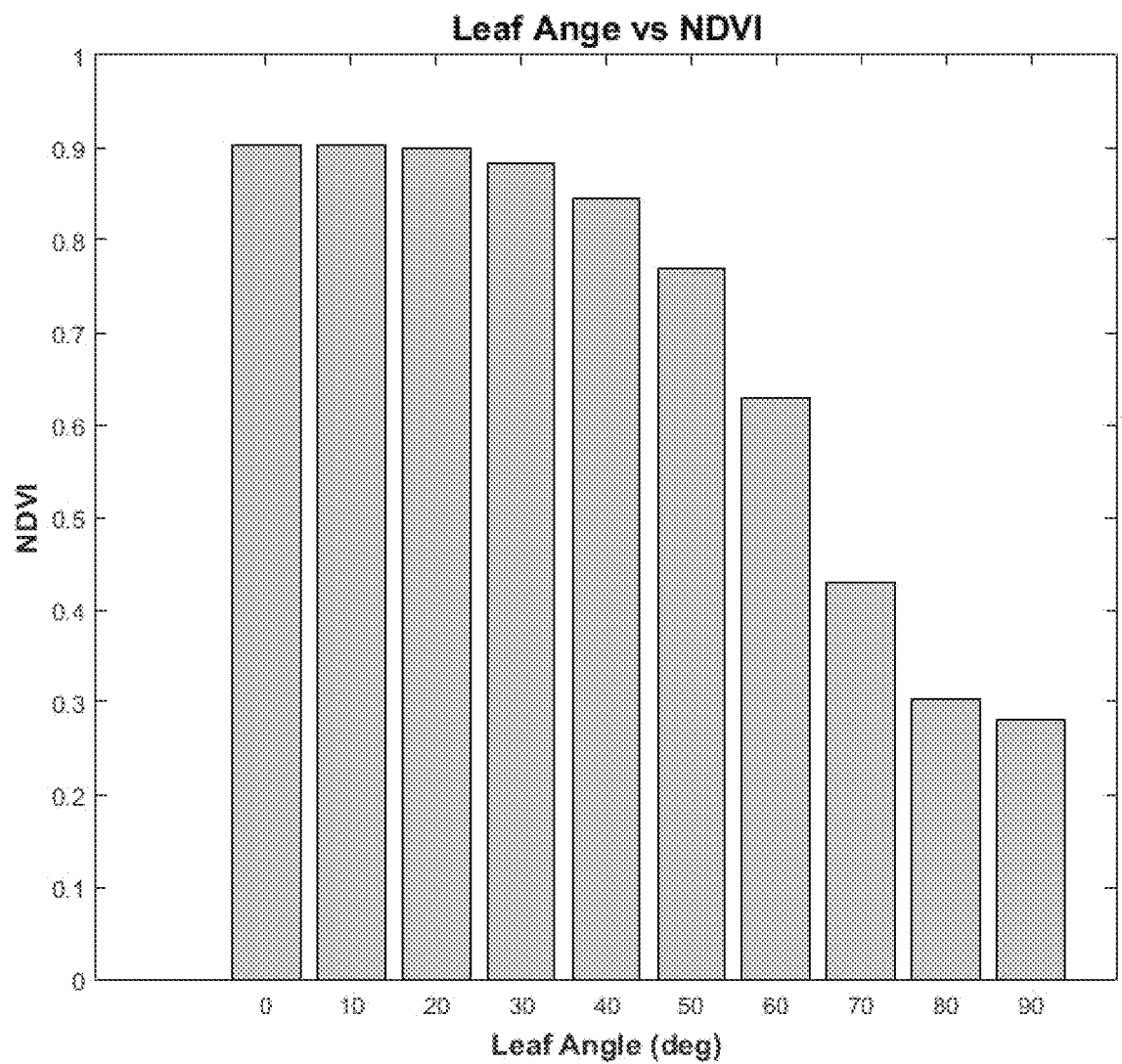
FIG. 8 illustrates a graph that further demonstrates that rotating the leaf from 0 degree to 80 degrees to the camera's normal direction causes 3 times (300%) change to the NDVI (normalized difference vegetation index) measurement.

The distance, and direction between the camera and object significantly impact the imaging results. Therefore, these parameters need to be fixed and optimized for uniform and high quality plant features measurement to be achieved. FIGS. 4, 5 and 6 show a leaf holder attachment according to one embodiment which holds a leaf sample at a fixed distance and angle with respect to the smartphone camera or lens system. As shown in FIG. 7, the relative angle between the leaf surface (e.g., from 0 degrees to 80 degrees) and the camera's normal direction significantly changes the spectral data in the image. FIG. 8 further demonstrates that rotating the leaf from 0 degree to 80 degrees to the camera's normal direction causes 3 times (300%) change to the NDVI (normalized difference vegetation index) measurement.

To allow the device to operate in both indoor and outdoor conditions, with various/changing lighting condition, calibration is provided to ensure useful and steady measurements. In certain embodiments, the smartphone attachment incorporates a white reference portion. The leaf holder board includes two portions. The upper portion includes a leaf-retaining mechanism, such as a clamp, while the lower half is the white reference for calibrating the color balance. In other embodiments, the upper portion may comprise the white reference and the lower portion may comprise the leaf holding mechanism. In at least one embodiment, the white reference portion includes at least one of white poly-vinylchloride, spectrolon, a material reflecting above 97% of light, wherein the light has a wavelength ranging between 400 nm (nanometers) and 1000 nm, or polytetrafluoroethylene.

In other embodiments, the white reference portion can be implemented to surround the sample mounting portion. In such embodiments, the virtual white reference intensity at any point P may be calculated as $intensity_P = intensity_X * intensity_Y / intensityO$, where O is the origin, and X and Y are the coordinates in the plane of view. The white reference portion is installed or formed at the fixed position on the sample mounting portion so there is no need to redo the white area searching a leaf segmentation for each imaging occurrence. The leaf's color intensity is at point P is then calibrated as the raw color divided by $intensity_P$.

In certain embodiments, the camera receives 3 RGB colors and 3 NIR bands, which are then used to predict nitrogen content in the sample. The one example, these six bands are combined using the following equation to determine the nitrogen content: 0.123*B+0.238*G+0.178*R+0.313*(NIR filtered B)+0.513*(NIR filtered G)+0.604*(NIR filtered R).

Figure 9:
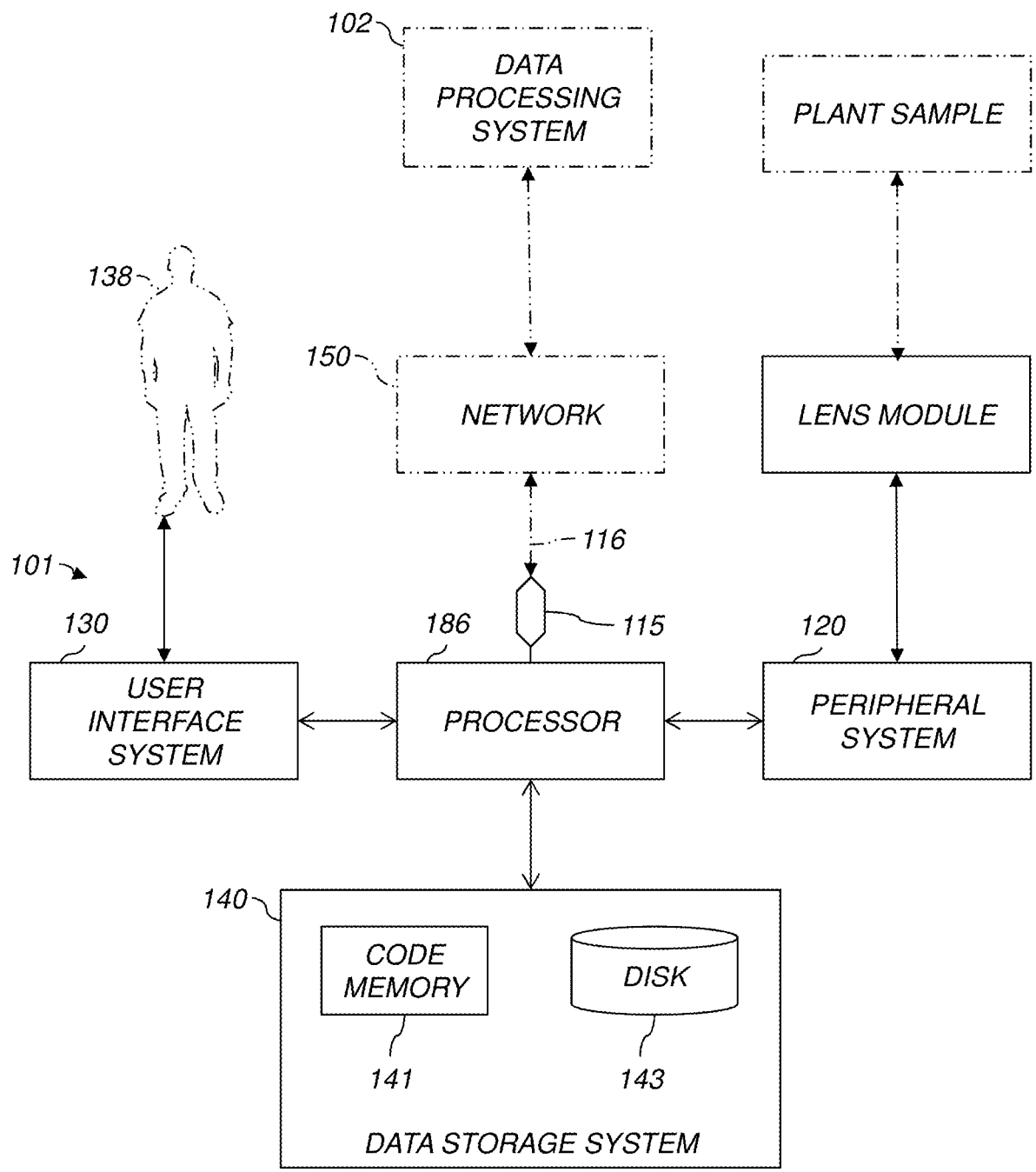
FIG. 9 is a high-level diagram showing the components of the one example of the system 100 for analyzing data and performing other analyses described herein, and related components.

FIG. 9 is a high-level diagram showing the components of one example of the system 100 for analyzing data and performing other analyses described herein, and related components. The system 100 includes a processor 186, a peripheral system 120, a user interface system 130, and a data storage system 140. The peripheral system 120, the user interface system 130 and the data storage system 140 are communicatively connected to the processor 186. Processor 186 can be communicatively connected to network 150 (shown in phantom), e.g., the Internet or a leased line, as discussed below. It shall be understood that the system 120 may include multiple processors 186 and other components shown in FIG. 9. The plant health data described herein may be obtained using network 150 (from one or more data sources), peripheral system 120 and/or displayed using display units (included in user interface system 130) which can each include one or more of systems 186, 120, 130, 140, and can each connect to one or more network(s) 150. Processor 186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 186 can implement processes of various aspects described herein. Processor 186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical magnetic, optical, biological components, or otherwise. Processor 186 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 120, user interface system 130, and data storage system 140 are shown separately from the data processing system 186 but can be stored completely or partially within the data processing system 186.

The peripheral system 120 can include one or more devices configured to provide digital content records to the processor 186. For example, the peripheral system 120 can include cellular phones (with a leaf holder mounted thereto, as shown in FIGS. 4, 5, and 6) or other data processors. The processor 186, upon receipt of digital content records from a device in the peripheral system 120, can store such digital content records in the data storage system 140.

The user interface system 130 can include a mouse, a keyboard, another computer (connected. e.g., via a network or a null-modem cable), or any device or combination of devices from which data is input to the processor 186. The user interface system 130 also can include a display device, a processor-accessible memory, or any device or combination of devices to which data is output by the processor 186. The user interface system 130 and the data storage system 140 can share a processor-accessible memory.

In various aspects, processor 186 includes or is connected to communication interface 115 that is coupled via network link 116 (shown in phantom) to network 150. For example, communication interface 115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link. e.g., WiFi or GSM. Communication interface 115 sends and receives electrical, electromagnetic or optical signals that carry digital or analog data streams representing various types of information across network link 116 to network 150. Network link 116 can be connected to network 150 via a switch, gateway, hub, router, or other networking device.

Processor 186 can send messages and receive data, including program code, through network 150, network link 116 and communication interface 115. For example, a server can store requested code for an application program (e.g., a JAVA applet) on a tangible non-volatile computer-readable storage medium to which it is connected. The server can retrieve the code from the medium and transmit it through network 150 to communication interface 115. The received code can be executed by processor 186 as it is received, or stored in data storage system 140 for later execution.

Data storage system 140 can include or be communicatively connected with one or more processor-accessible memories configured to store information. The memories can be, e.g., within a chassis or as parts of a distributed system. The phrase "processor-accessible memory" is intended to include any data storage device to or from which processor 186 can transfer data (using appropriate components of peripheral system 120), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes. Compact Discs, DVDs, read-only memories (ROM), erasable programmable read-only memories (EPROM, EEPROM, or Flash), and random-access memories (RAMs). One of the processor-accessible memories in the data storage system 140 can be a tangible non-transitory computer-readable storage medium, i.e., a non-transitory device or article of manufacture that participates in storing instructions that can be provided to processor 186 for execution.

In an example, data storage system 140 includes code memory 141, e.g., a RAM, and disk 143, e.g., a tangible computer-readable rotational storage device such as a hard drive. Computer program instructions are read into code memory 141 from disk 143. Processor 186 then executes one or more sequences of the computer program instructions loaded into code memory 141, as a result performing process steps described herein. In this way, processor 186 carries out a computer implemented process. For example, steps of methods described herein, blocks of the flowchart illustrations or block diagrams herein, and combinations of those, can be implemented by computer program instructions. Code memory 141 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 186 (and possibly also other processors), to cause functions, acts, or operational steps of various aspects herein to be performed by the processor 186 (or other processor). Computer program code for carrying out operations for various aspects described herein may be written in any combination of one or more programming language(s), and can be loaded from disk 143 into code memory 141 for execution. The program code may execute, e.g., entirely on processor 186, partly on processor 186 and partly on a remote computer connected to network 150, or entirely on the remote computer.

The invention is inclusive of combinations of the aspects described herein. References to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. An imaging system for a smartphone, comprising:
   a housing configured to rigidly attach to a handheld smartphone device;
   an arm extending from the housing;
   a sample mounting portion attached to the arm, the mounting portion having a retaining device for securing a plant sample to the mounting portion, the mounting portion configured to direct an image of the plant sample to a first camera in the handheld smartphone device; and
   at least one mirror mounted to the housing, the mirror configured to direct an image of the plant sample to a second camera in the handheld smartphone device, the second camera located on an opposite side of the handheld smartphone device as the first camera.

2. The imaging system of claim 1, wherein the mounting portion further includes a white reference portion for calibrating the image.

3. The imaging system of claim 2, wherein the white reference portion comprises at least one of white poly-vinyl-chloride, Spectralon, or Polytetrafluoroethylene.

4. The imaging system of claim 1, wherein the arm is configured to be adjustable such that the arm is movable toward and away from the housing.

5. The imaging system of claim 1, further comprising a lens module having a slideable housing, the slidable housing configured to move between a first lens position and the second lens position as an image is captured.

6. The imaging system of claim 5, wherein the first lens position exposes the first camera to the plant sample.

7. The imaging system of claim 5, wherein the second lens position prevents exposure of the first camera to the plant sample.

8. The imaging system of claim 1, further comprising a lens module having three lenses which simultaneously direct three corresponding images of the sample to the camera.

9. The imaging system of claim 1, further comprising a color band filter which provides a low-pass filter of light, the low-pass filter having a cutoff which is between 700 nm and 720 nm.

10. An imaging system for a smartphone, comprising:
    a housing configured to rigidly attach to a handheld smartphone device;
    an arm extending from the housing;
    a sample mounting portion attached to the arm, the mounting portion having a retaining device, wherein the retaining device is configured to secure a target sample, the mounting portion configured to direct an image of the target sample to a first camera in the handheld smartphone device; and
    a lens module having at least three lenses, wherein each lens of the at least three lenses simultaneously direct multiple images of the target sample to the camera.

11. The imaging system of claim 10, wherein the arm is configured to be adjustable such that the arm is movable toward and away from the housing.

12. The imaging system of claim 10, wherein the lens module further comprises replaceable color filters, wherein each replaceable color filter corresponds to each lens of the at least three lenses.

13. An imaging system for a smartphone, comprising:
    a housing configured to rigidly attach to a handheld smartphone device;
    an arm extending from the housing, wherein the arm is configured to be adjustable such that the arm is movable toward and away from the housing;
    a sample mounting portion attached to the arm, the mounting portion having a retaining device, wherein the retaining device is configured to secure a target sample, the mounting portion configured to direct an image of the target sample to a first camera in the handheld smartphone device; and
    a lens module having at least three lenses, wherein each lens of the at least three lenses simultaneously direct multiple images of the target sample to the camera.

14. The imaging system of claim 13, further comprising:
    at least one mirror mounted to the housing, the mirror configured to direct an image of the target sample to a second camera in the handheld smartphone device, the second camera located on an opposite side of the handheld smartphone device as the first camera.

15. The imaging system of claim 14, further comprising a lens module having a slideable housing, the slidable housing configured to move between a first lens position and the second lens position.

16. The imaging system of claim 15, wherein the mounting portion further includes a white reference portion.

17. The imaging system of claim 16, wherein the white reference portion comprises at least one of white poly-vinyl-chloride, Spectralon, or Polytetrafluoroethylene.

* * * * *